US012636383B2

(12) United States Patent
Korczykowski

(10) Patent No.: US 12,636,383 B2
(45) Date of Patent: May 26, 2026

(54) METHODS OF APPLYING PREPARATIONS OF DYES AND HYDROGELS TO A TISSUE

(71) Applicant: Marc Korczykowski, New York, NY (US)

(72) Inventor: Marc Korczykowski, New York, NY (US)

(*) Notice: Subject to any disclaimer, the term of this patent is extended or adjusted under 35 U.S.C. 154(b) by 585 days.

(21) Appl. No.: 16/632,012

(22) PCT Filed: Jul. 18, 2018

(86) PCT No.: PCT/US2018/042675
§ 371 (c)(1),
(2) Date: Jan. 17, 2020

(87) PCT Pub. No.: WO2019/018520
PCT Pub. Date: Jan. 24, 2019

(65) Prior Publication Data
US 2020/0230260 A1 Jul. 23, 2020

Related U.S. Application Data

(60) Provisional application No. 62/533,977, filed on Jul. 18, 2017.

(51) Int. Cl.
| | |
|---|---|
| A61K 49/00 | (2006.01) |
| A61B 5/00 | (2006.01) |
| A61B 5/24 | (2021.01) |
| A61B 17/16 | (2006.01) |
| A61B 90/00 | (2016.01) |

(52) U.S. Cl.
CPC .............. *A61K 49/006* (2013.01); *A61B 5/24* (2021.01); *A61B 5/6868* (2013.01); *A61K 49/0034* (2013.01); *A61K 49/0043* (2013.01); *A61K 49/0073* (2013.01); *A61B 17/1695* (2013.01); *A61B 2090/3933* (2016.02); *A61B 2090/3937* (2016.02); *A61B 2503/40* (2013.01); *A61B 2562/0217* (2017.08)

(58) Field of Classification Search
CPC .......... A61K 49/00; A61B 5/24; A61B 5/6868
See application file for complete search history.

(56) References Cited

U.S. PATENT DOCUMENTS

| | | | | |
|---|---|---|---|---|
| 7,273,896 | B2 * | 9/2007 | Daniloff | A61L 31/14 |
| | | | | 522/74 |
| 2012/0264078 | A1 | 10/2012 | Patel et al. | |
| 2014/0174724 | A1 | 6/2014 | Livanec et al. | |

FOREIGN PATENT DOCUMENTS

| | | | |
|---|---|---|---|
| WO | 2009/058134 A1 | | 5/2009 |
| WO | WO 2009/058134 | * | 5/2009 |

OTHER PUBLICATIONS

Isabella Ferezou et al. Chapter 6, Imaging the Brain in action: Real-Time Voltage-Sensitive Dye Imaging of Sensooimotor Cortex of Aswake Behaving Mice, NCBI Bookshelf. (Year: 2009).*
Wen-Biao Gan et al. Multicolor "DiOlistic"Labeling of the Nervous System Using Lipophilic Dye Combinations, Neuron,27,219-225. (Year: 2000).*
James J. DiCarlo et al., Marking microelectrode penetrations with fluorescent dyes, J. Neuroscience Methods, 64,75-81. (Year: 1996).*
Truett Allison et al., Electrophysiological studies of color processing in human visual cortex, Electroencephalography and Clinical Neurophysiology, 88, 343-355. (Year: 1993).*
N. Jeremy Hill et al., Recording Human Electrocorticographic (ECOG) Signals for Neuroscientific Research and Real-time Functional Cortical Mapping, J of Visualized Experiments, 64, e3993, 1-5. (Year: 2012).*
James J DeCarlo et al., Marking microelectrode penetrations with fluorescent dyes, J. Neuroscience Methods, 64, 75-81. (Year: 1996).*
International Search Report mailed Nov. 14, 2018, issued in connection with PCT International Application No. PCT/US2018/042675.
Written Opinion issued in connection with PCT International Application No. PCT/US2018/042675.
International Preliminary Report on Patentability, issued Jan. 21, 2020, in connection with PCT International Application No. PCT/US2018042675.
Oikawa et al., "A Fine-Scale and Minimally Invasive Marking Method for Use with Conventional Tungsten Microelectrodes", ENEURO, 2023, 10(9), pp. 1-12.

* cited by examiner

*Primary Examiner* — Michael G. Hartley
*Assistant Examiner* — Jagadishwar R Samala
(74) *Attorney, Agent, or Firm* — Hoxie & Associates LLC

(57) ABSTRACT

Disclosed is a marking composition comprising a marker and a hydrogel. Disclosed is a process of forming a marking composition comprising mixing a marker and a hydrogel. Disclosed is an article comprising a marker, a hydrogel, and an implement. Disclosed is a kit comprising a marker, a hydrogel, and an implement, wherein the marker and hydrogel are combined. Disclosed is a method for marking a portion of the brain in a mammal comprising: (a) removing a portion of a mammal's skull to expose a portion of the brain matter; and (b) contacting the exposed portion of the brain with a marking composition. Disclosed is a method for recording electrical activity in a brain, comprising: (a) removing a portion of the skull, thereby exposing a portion of a brain; (b) inserting an electrode into the brain; and (c) recording electrical activity via the electrode, wherein the electrode is at least partially coated with a marking composition.

14 Claims, No Drawings

METHODS OF APPLYING PREPARATIONS OF DYES AND HYDROGELS TO A TISSUE

This application is a § 371 national stage of PCT International Application No. PCT/US2018/042675, filed Jul. 18, 2018, which claims the benefit of U.S. Provisional Patent Application No. 62/533,977, filed Jul. 18, 2017, the entire disclosures of each of which are incorporated herein by reference.

BACKGROUND OF THE DISCLOSURE

Techniques such as magnetic resonance imaging are capable of providing exquisite detail of brain structure and anatomy. This is can be extremely valuable in surgery, which involves the placement of electrodes and clinical diagnostic devices at precise locations in tissue.

During neurosurgical procedures involving craniotomy, during which time a part of the skull is removed to access the brain tissue, brain edema and deformation of the brain may occur, as well as the 'midline shift' that involves an alteration in the brain's spatial orientation. These conditions can render any pre-craniotomy imaging of questionable valuable. Therefore, there exists a long felt but unsolved need for the placement of materials at precise places in the brain such that their location remains true to the pre-craniotomy structure. The placement of these materials maintains the pre-surgical clinical and diagnostic information and improves the localization and precision of surgical outcomes.

BRIEF SUMMARY OF THE DISCLOSURE

Disclosed is a marking composition comprising a marker and a hydrogel.

Disclosed is a marking composition, wherein the marker comprises a colored dye.

Disclosed is a marking composition, wherein the colored dye is selected from the group consisting of methylene blue, indigo carmine, fluorescein, and indocyanine green.

Disclosed is a marking composition, wherein the ratio of the colored dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a marking composition, wherein the marker comprises a colorless dye.

Disclosed is a marking composition, wherein the ratio of the colorless dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a marking composition, wherein a base material of the hydrogel comprises a polymer selected from the group consisting of silicone, polyacrylamide, polymacon, polyethylene oxide, poly(2-acrylamido-2-methyl-1-propanesulfonicacid), polyvinyl-pyrrolidone, and alginate.

Disclosed is a marking composition, wherein the hydrogel comprises more than one base material.

Disclosed is a process of forming a marking composition comprising mixing a marker and a hydrogel.

Disclosed is an article comprising a marker, a hydrogel, and an implement.

Disclosed is an article, wherein the marker comprises a colored dye.

Disclosed is an article, wherein the colored dye is selected from the group consisting of methylene blue, indigo carmine, fluorescein, and indocyanine green.

Disclosed is an article, wherein the ratio of the colored dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is an article, wherein the marker comprises a colorless dye.

Disclosed is an article, wherein the ratio of the colorless dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is an article, wherein a base material of the hydrogel comprises a polymer selected from the group consisting of silicone, polyacrylamide, polymacon, polyethylene oxide, poly(2-acrylamido-2-methyl-1-propanesulfonicacid), polyvinyl-pyrrolidone, and alginate.

Disclosed is an article, wherein the hydrogel comprises more than one base material.

Disclosed is an article, wherein the implement is selected from the group consisting of a stylus, a needle, a brush, and a pen.

Disclosed is a kit comprising a marker, a hydrogel, and an implement, wherein the marker and hydrogel are combined.

Disclosed is a kit, wherein the marker comprises a colored dye.

Disclosed is a kit, wherein the colored dye is selected from the group consisting of methylene blue, indigo carmine, fluorescein, and indocyanine green.

Disclosed is a kit, wherein the ratio of the colored dye to the hydrogel is selected from the group consisting of 10,000: 1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a kit, wherein the marker comprises a colorless dye.

Disclosed is a kit, wherein the ratio of the colorless dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a kit, wherein a base material of the hydrogel comprises a polymer selected from the group consisting of silicone, polyacrylamide, polymacon, polyethylene oxide, poly(2-acrylamido-2-methyl-1-propanesulfonicacid), poly-vinyl-pyrrolidone, and alginate.

Disclosed is a kit, wherein the hydrogel comprises more than one base material.

Disclosed is a kit, wherein the implement is selected from the group consisting of a stylus, a needle, a brush, and a pen.

Disclosed is a method for marking a portion of the brain in a mammal comprising: (a) removing a portion of a mammal's skull to expose a portion of the brain matter; and (b) contacting the exposed portion of the brain with a marking composition.

Disclosed is a method, wherein the marking composition comprises a marker and a hydrogel.

Disclosed is a method, wherein the marker comprises a colored dye.

Disclosed is a method, wherein the colored dye is selected from the group consisting of methylene blue, indigo carmine, fluorescein, and indocyanine green.

Disclosed is a method, wherein the ratio of the colored dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a method, wherein the marker comprises a colorless dye.

Disclosed is a method, wherein the ratio of the colorless dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a method, wherein a base material of the hydrogel comprises a polymer selected from the group consisting of silicone, oxide, polyacrylamide, polymacon, polyethylene oxide, poly(2-acrylamido-2-methyl-1-propanesulfonicacid), polyvinyl-pyrrolidone, and alginate.

Disclosed is a method, wherein the hydrogel comprises more than one base material.

Disclosed is a method, wherein the mammal's skull is selected from the group consisting of a mouse skull, a rat skull, bovine skull, an ovine skull, an equine skull, a primate skull, a chimpanzee skull, and a human skull.

Disclosed is a method, wherein the mammal's skull is a human skull.

Disclosed is a method, wherein removing the portion of the mammal's skull comprises a craniotomy.

Disclosed is a method, wherein the portion of the mammal's skull is selected from the group consisting of an occipital bone, a temporal bone, a parietal bone, a sphenoid bone, an ethmoid bone, and a frontal bone.

Disclosed is a method, wherein the portion of the brain matter is selected from the group consisting of a frontal lobe, a parietal lobe, a temporal lobe, or a occipital lobe.

Disclosed is a method, wherein the contacting is with an implement selected from the group consisting of a stylus, a needle, a brush, and a pen.

Disclosed is a method for recording electrical activity in a brain, comprising: (a) removing a portion of the skull, thereby exposing a portion of a brain; (b) inserting an electrode into the brain; and (c) recording electrical activity via the electrode, wherein the electrode is at least partially coated with a marking composition.

Disclosed is a method, wherein the marking composition comprises a marker and a hydrogel.

Disclosed is a method, wherein the marker comprises a colored dye.

Disclosed is a method, wherein the colored dye is selected from the group consisting of methylene blue, indigo carmine, fluorescein, and indocyanine green.

Disclosed is a method, wherein the ratio of the colored dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a method, wherein the marker comprises a colorless dye.

Disclosed is a method, wherein the ratio of the colorless dye to the hydrogel is selected from the group consisting of 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis.

Disclosed is a method, wherein a base material of the hydrogel comprises a polymer selected from the group consisting of silicone, polyacrylamide, polymacon, polyethylene oxide, poly(2-acrylamido-2-methyl-1-propanesulfonicacid), polyvinyl-pyrrolidone, and alginate.

Disclosed is a method, wherein the hydrogel comprises more than one base material.

Disclosed is a method, wherein the skull is selected from the group consisting of a mouse skull, a rat skull, bovine skull, an ovine skull, an equine skull, a primate skull, a chimpanzee skull, and a human skull.

Disclosed is a method, wherein the skull is a human skull.

Disclosed is a method, wherein removing the portion of the skull comprises a craniotomy.

Disclosed is a method, wherein the portion of the skull is selected from the group consisting of an occipital bone, a temporal bone, a parietal bone, a sphenoid bone, an ethmoid bone, and a frontal bone.

Disclosed is a method, wherein the portion of the brain is selected from the group consisting of a frontal lobe, a parietal lobe, a temporal lobe, or a occipital lobe.

Disclosed is a method, wherein the contacting is with an implement selected from the group consisting of a stylus, a needle, a brush, and a pen.

DETAILED DESCRIPTION OF THE DISCLOSURE

"Markers," as disclosed herein, may be colored dyes or colorless dyes.

A "colored dye," as disclosed herein, refers to a substance having an affinity to the substrate to which it is applied and having an emission spectrum overlapping the visible spectrum. Non-limiting examples of colored dyes are methylene blue, indigo carmine, fluorescein, and indocyanine green. A "colorless dye," as disclosed herein, refers to a substance having an affinity to the substrate to which it is applied which does not necessarily have an emission spectrum overlapping the visible spectrum.

It is understood that the definition of "colored dyes" includes substances covalently attached to the colored dyes, wherein these substances are responsible for the affinity for the substrate. A non-limiting example of a substance responsible for the affinity for the substrate is the isothiocyanate moiety in fluorescein isothiocyanate. Further further non-limiting examples of a substance responsible for the affinity for the substrate are antibodies or fragments thereof.

A "hydrogel," as disclosed herein, refers to a network of polymer chains that are hydrophilic. The disclosed hydrogels have at least one "base material." Non-limiting examples of the bases of hydrogels are silicone, polyacrylamide, polymacon, polyethylene oxide, poly(2-acrylamido-2-methyl-1-propanesulfonicacid), polyvinyl-pyrrolidone, and alginate. A hydrogel may have more than one base material.

The ratio of the colored dye to the hydrogel is from 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis. The ratio of the colorless dye to the hydrogel is from 10,000:1, 5,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight:weight basis. By "weight:weight basis," it is meant that the ratio is based on a comparison of the dry weight of the marker to the dry weight of the hydrogel. All ranges of ratios between 10,000:1 to 10,000:1 on a weight:weight basis are disclosed. By way of a non-limiting example, the range 5:1 on a weight:weight basis to 1:5 on a weight:weight basis is disclosed.

Disclosed is a marking composition comprising a marker and a hydrogel.

Disclosed is an article comprising a marker, a hydrogel, and an implement. The implement can be a stylus, a needle, a brush, or a pen. The marker and hydrogel can be located on the tip of the implement or on the bristles of the brush. The marker and hydrogel can also be located on a shaft of the implement.

Disclosed is a kit comprising a marker, a hydrogel, and an implement, wherein the marker and hydrogel are combined.

Disclosed is a method for marking a portion of the brain in a mammal comprising: (a) removing a portion of a mammal's skull to expose a portion of the brain matter; and (b) contacting the exposed portion of the brain with a marking composition.

The removal of the portion of the skull can be temporary or permanent, although most cases are temporary. If the removal of the skull portion is temporary, the removal is conducted so as to avoid as much damage as possible to the brain structure or vasculature. The temporary removal of the portion of the skull can be conducted by drilling. The portion of the skull removed can be as small as 1 mm$^2$ or as large as an occipital bone, a temporal bone, a parietal bone, a sphenoid bone, an ethmoid bone, or a frontal bone.

The implement may be an electrode or an electronic device.

The implement may be capable of two-way interactions with one or more interfaces. In such implements, information can be relayed to an interface or from an interface to drive, train, or modulate the cells of a mammal. This relay of information may cause the formation of a feedback loop that regulates or programs the biological parameter. In some such interfaces, the information relayed is or has been subject to a feedback loop. Some interfaces may be electrical interfaces. The interfaces can be capable of converting two-dimensional information into three-dimensional information, and three-dimensional information into four-dimensional information.

What is claimed is:

1. A method for marking an anatomical location on an exposed portion of a human brain, comprising:
   a) removing a portion of a human skull to expose a portion of a brain;
   b) contacting an anatomical location to be marked with an electrode, wherein the electrode is at least partially coated with a hydrogel marking composition comprising a colored dye selected from the group consisting of methylene blue, indigo carmine, fluorescein, and indocyanine green, thereby marking the anatomical location with the hydrogel marking composition;
   c) recording electrical activity in the marked anatomical location via the electrode; and
   d) removing the electrode,
   wherein the hydrogel marking composition is located on the tip of the electrode.

2. The method of claim 1, wherein the ratio of the colored dye to the hydrogel is selected from the group consisting of 10,000:1, 1,000:1, 4,000:1, 3,000:1, 2,000:1, 1,000:1, 500:1, 250:1, 125:1, 100:1, 75:1, 50:1, 40:1, 30:1, 25:1, 20:1, 15:1, 10:1, 5:1, 4:1, 3:1, 2:1, 1:1, 1:2, 1:3, 1:4, 1:5, 1:10, 1:20, 1:25, 1:30, 1:40, 1:50, 1:75, 1:100, 1:125, 1:250, 1:500, 1:1,000, 1:2,000, 1:3,000, 1:4,000, 1:5,000, and 1:10,000 on a weight: weight basis.

3. The method of claim 1, wherein a base material of the hydrogel comprises a polymer selected from the group consisting of silicone, polyacrylamide, polymacon, polyethylene oxide, poly(2-acrylamido-2-methyl-1-propanesulfonicacid), polyvinyl-pyrrolidone, and alginate.

4. The method of claim 1, wherein the hydrogel comprises more than one base material.

5. The method of claim 1, wherein removing the portion of the skull comprises a craniotomy.

6. The method of claim 1, wherein the portion of the skull is selected from the group consisting of an occipital bone, a temporal bone, a parietal bone, a sphenoid bone, an ethmoid bone, and a frontal bone.

7. The method of claim 1, wherein the portion of the brain is selected from the group consisting of a frontal lobe, a parietal lobe, a temporal lobe, and an occipital lobe.

8. The method of claim 1, wherein the contacting is with an implement selected from the group consisting of a stylus, a needle, a brush, and a pen.

9. The method of claim 1, further comprising stimulating electrical activity in the anatomical location via the electrode.

10. The method of claim 9, wherein the stimulation drives, trains, and/or modulates at least one cell within the anatomical location.

11. The method of claim 9, wherein the recordation and stimulation form a feedback loop.

12. The method of claim 11, wherein the feedback loop regulates or programs a biological parameter.

13. The method of claim 1, further comprising conducting surgery at the anatomical location.

14. A method for marking an anatomical location on an exposed portion of a human brain comprising:
   a) removing a portion of a human skull to expose a portion of a brain;
   b) contacting an anatomical location to be marked with an electrode, wherein the electrode is at least partially coated with a hydrogel marking composition comprising a colored dye selected from the group consisting of methylene blue, indigo carmine, fluorescein, and indocyanine green, thereby marking the anatomical location with the hydrogel marking composition;

c) stimulating electrical activity in the marked anatomical location via the electrode; and d) removing the electrode, wherein the hydrogel marking composition is located on the tip of the electrode.

* * * * *